US00PP23570P2

(12) United States Plant Patent
Kordes

(10) Patent No.: US PP23,570 P2
(45) Date of Patent: Apr. 30, 2013

(54) HYBRID TEA ROSE PLANT NAMED 'KORSTEFLALI'

(50) Latin Name: *Rosa hybrida*
Varietal Denomination: KORsteflali

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/136,224

(22) Filed: Jul. 25, 2011

(51) Int. Cl.
*A01H 5/00* (2006.01)

(52) U.S. Cl. ..... Plt./137

(58) Field of Classification Search ..... Plt./137, Plt./138

See application file for complete search history.

*Primary Examiner* — Kent L Bell

(57) ABSTRACT

A new and distinct variety of rose with large, novel pink flowers, and attractive foliage with excellent disease resistance. It exhibits vigorous growth and an upright habit. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORsteflali'.

The new variety of rose plant of the present invention originated from a controlled crossing in a breeding program of two distinct parents during the summer of 2001. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORsteflali'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. The flower color of 'KORsteflali' is pink while the flower color of the seed parent is violet pink.
2. The petal count of 'KORsteflali' is very double while the petal count of the seed parent is semi-double.

The new rose plant may be distinguished from its pollen parent, an 'un-named seedling' by the following combination of characteristics:

1. The flower bud of 'KORsteflali' is a pointed ovoid while the flower bud shape of the pollen parent is round.
2. The growth habit of 'KORsteflali' is upright to bushy while the growth habit of the pollen parent is tall.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORsteflali' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORsteflali' was selected in May, 2002 from the seedling beds to be asexually propagated for further evaluation. The first asexual propagation of 'KORsteflali' was done by budding to seedling understocks in July, 2002 at the inventor's nursery in Offenseth-Sparrieshoop, Germany.

This initial and other subsequent propagations conducted in controlled environments demonstrate that 'KORsteflali' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORsteflali'.

DETAILED BOTANICAL DESCRIPTION

The following is a description of 'KORsteflali', as observed growing in July, 2011 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORpauvio', a rose variety from the same inventor described and illustrated in U.S. Plant patent application Ser. No. 12/799,526 and filed on Apr. 26, 2010 are compared to 'KORsteflali' in Chart 1.

CHART 1

| Characteristic | 'KORsteflali' | 'KORpauvio' |
|---|---|---|
| Flower bud form: | Long. Pointed ovoid. | Short and globular. |
| Petal reflex: | Limited petal reflex. | Strong petal reflex. |
| Stamens: | 40-50 on average. | 70-80 on average. |

Parents:

*Seed parent*.—An 'un-named seedling'.

*Pollen parent*.—An 'un-named seedling'.

Classification:

*Botanical classification*.—*Rosa hybrida* 'KORsteflali'.

*Commercial classification*.—Hybrid Tea rose.

FLOWER AND FLOWER BUD

Blooming habit: Recurrent.

Flower bud:

*Size*.—Upon opening, 35 mm in length from base of receptacle to end of bud and 25 mm diameter at its widest point.

*Bud form*.—Long. Pointed ovoid.

*Bud color*.—As sepals first unfold, bud color is Red-Purple Group N57A. When ¼ open, the upper surface of petals is Red-Purple Group 157C, and the lower surface is Red-Purple Group 62C and 62D in the basal and middle zones and Red-Purple Group N57B in the marginal zone. Guard petals are Red-Purple Group 59B and 59C.

Sepals:

*Color*.—Upper surface Yellow-Green Group 144D. Lower surface Yellow-Green Group 144B suffused with Greyed-Purple Group 183D.

*Size*.—Average 35 mm (l)×15 mm (w).

*Shape*.—Triangular. Foliaceous appendages lacking. Apex: Apiculate. Base: Flat at union with receptacle.

*Quantity*.—Five.

*Surface texture*.—Upper side: Very pubescent. Lower surface: Rough with light pubescence.

*Margins*.—Pubescent, stipitate glands generally lacking.

Receptacle:

*Surface*.—Smooth.

*Color*.—Yellow-Green Group 144B.

*Shape*.—Urn-shaped.

*Size*.—12-15 mm (h)×15-18 mm (w).

Peduncle:

*Surface*.—With limited numbers of stipitate glands.

*Length*.—65 to 80 mm average length.

*Diameter*.—4 to 6 mm average diameter.

*Color*.—Yellow-Green Group 144B.

*Strength*.—Strong.

*Borne*.—Singly.

*Anthocyanin*.—Greyed-Purple Group 183D.

Flower bloom:

*Fragrance*.—Moderate.

*Duration*.—On the plant 5 to 7 days. As a cut flower, 4 to 5 days. Senesced petals drop away.

*Size*.—Large. When open, the average flower diameter is 100 mm and the average flower height is 50-60 mm.

*Form*.—Shape of flower when viewed from the side: Upon opening, upper part: Flat. Upon opening, lower part: Flattened convex. Open flower, upper part: Flat. Open flower, lower part: Flattened convex.

Color:

*Upon opening, petals*.—Outermost petals: Outer Side: Red-Purple Group 62D with marginal zone Red-Purple Group N57B. Inner Side: Red-Purple Group 62B with marginal zone Red-Purple Group N57D. Innermost petals: Outer Side: Red-Purple Group N57D with marginal zone Red-Purple Group 63B. Inner Side: Red Group 50D with marginal zone 54B.

*Upon opening, basal petal spots*.—Basal petal spot, outermost petals: Outer Side: Green-Yellow Group 1B. Inner Side: Green-Yellow Group 1A. Basal petal spot, innermost petals: Outer Side: Green-Yellow Group 1A. Inner Side: Yellow Group 2B.

*After opening, petals*.—Outermost petals: Outer Side: Red-Purple Group 62D with marginal zone 63C. Inner Side: Red-Purple Group 62D with marginal zone 63C and 63D. Innermost petals: Outer Side: Red-Purple Group 63C and 63D. Inner Side: Red-Purple Group 62C.

*After opening, basal petal spots*.—Basal petal spot, outermost petals: Outer Side: Green-Yellow Group 1C. Inner Side: Green-Yellow Group 1D. Basal petal spot, innermost petals: Outer Side: Green-Yellow Group 1D. Inner Side: Green-Yellow Group 1D.

General tonality: On open flower Red-Purple Group 63C and 63D. No change in the general tonality at the end of the 4$^{th}$ day. Afterwards, general tonality is Red-Purple Group 62C and 62D.

Petals:

*Petal count*.—Very double. Average Range: Approximately 40-50 petals under normal conditions.

*Petal reflex*.—Petals reflex somewhat.

*Petal edge*.—Entire.

*Petal shape*.—Obtuse. Apex shape is round. Shape of base is acute.

*Petal size*.—Average 50-60 mm (l)×40-50 mm (w).

*Thickness*.—Average.

*Petal arrangement*.—Not formal.

Petaloids: Usually a few present.

*Petaloid count*.—Average of 0-5 per flower.

*Petaloid size*.—Petaloids are 10 mm long and 4-8 mm wide.

*Petaloid color*.—Color of inner side is Red-Purple Group 63B. Color of outer side is Red-Purple Group 63B and 63C.

*Petaloid texture*.—Smooth.

*Margins*.—Entire.

*Petaloid shape*.—Irregular. Obovate to subulate.

Reproductive organs:

*Pistils*.—Abundant. Approximately 50 present. Stigmas: Location: Slightly inferior in position to anthers. Color: Yellow-Orange Group 18C with intonations of Red-Purple Group 58A. Styles: Length: Average 8-10 mm long. Color: Yellow-Green Group 145C.

*Stamens*.—Approximately 30 on average and regularly arranged. Anthers: Size: Average 4 mm long. Pollen: Generally present. Color: Yellow-Orange Group 20A. Filaments: Color: Red Group 46A. Length: Average 6-7 mm.

THE PLANT

Growth: Vigorous.

Plant habit: Upright habit. When grown as a budded field plant the height is 80 cm and the average width is 50 cm.

Stems:

*Stem color*.—Young wood: Yellow-Green Group 146C. Older wood: Yellow-Green Group 146A and 146B.

*Stem surface*.—Young wood: Smooth. Older wood: Smooth.

Prickles: Present.

*Incidence*.—Average 10-12 per each 10 cm of stem.

*Size*.—Average length: 8-10 mm.

*Color*.—Immature prickles: Greyed-Purple Group 182B and 182C. Mature prickles: Greyed-Brown Group 199B.

*Shape*.—Concave.

*Anthocyanin*.—Color Greyed-Purple Group 183B at base of juvenile thorns.

Leaves and leaflets: Normally 5 leaflets on normal leaves in middle of the stem.

*Venation pattern*.—Pyramidal net pattern.

*Leaf size*.—120 mm (l)×90 mm (w).

*Abundance*.—Average.

*Texture*.—Thick. Upper side of leaflet: Semi-glossy and smooth. Under side of leaflet: Matte and smooth.

*Color, mature foliage*.—Upper Leaf Surface: Green Group 137A. Lower Leaf Surface: Green Group 138A.

*Color, juvenile foliage*.—Upper Leaf Surface: Yellow-Green Group 146A. Lower Leaf Surface: Green Group 146B.

*Anthocyanin intonation*.—Present. Intonations present on juvenile, leaves and stems. Color is Greyed-Purple Group 183A and 183B.

Stipules:

*Size*.—Average 15 mm long. Average 5 mm between the tips of the stipules.

*Stipule color*.—Green Group 146C.

*Margins*.—With stipitate glands.

*Shape*.—Apex: Apiculate. Base: Winged.

Petiole:

*Length*.—Average 20-35 mm.

*Diameter*.—Average 2 mm.

*Petiole color*.—Yellow-Green Group 146C.

*Underneath*.—With prickles and slight pubescence.

*Margins*.—With stipitate glands.

Petiole rachis:

*Length*.—Average 20-35 mm.

*Diameter*.—Average 1-2 mm.

*Color*.—Yellow-Green Group 146C.

*Underneath*.—With prickles and slight pubescence.

*Margins*.—With stipitate glands and pubescence.

*Prickles*.—A few small prickles underneath.

*Stipitate glands*.—Stipitate glands on upper margins.

*Anthocyanin*.—On upper sides of juvenile leaflets. Color is Greyed-Purple Group 183B.

Leaflets:

*Size*.—Average size of the terminal leaflet is 55-60 mm (l)×40-45 mm (w).

*Shape*.—Entire leaflet: Ovate. Base: Obtuse. Apex: Acute.

*Margins*.—Finely serrated.

*Surface*.—Upper: Semi-glossy. Lower: Matte.

*Texture*.—Leathery.

*Arrangement*.—Pinnate.

*Venation*.—Reticulate.

Hips/seed formation: None observed.

Winter hardiness: To date, the variety has been grown successfully in Zones 5-9.

Disease resistance: Excellent resistance to powdery mildew (*Sphaerotheca pannosa*), blackspot (*Diplocarpon rosae*), and rust (*Phragmidium* sp.) diseases under normal growing conditions.

I claim:

1. A new and distinct variety of rose plant, as described and illustrated herein.

* * * * *

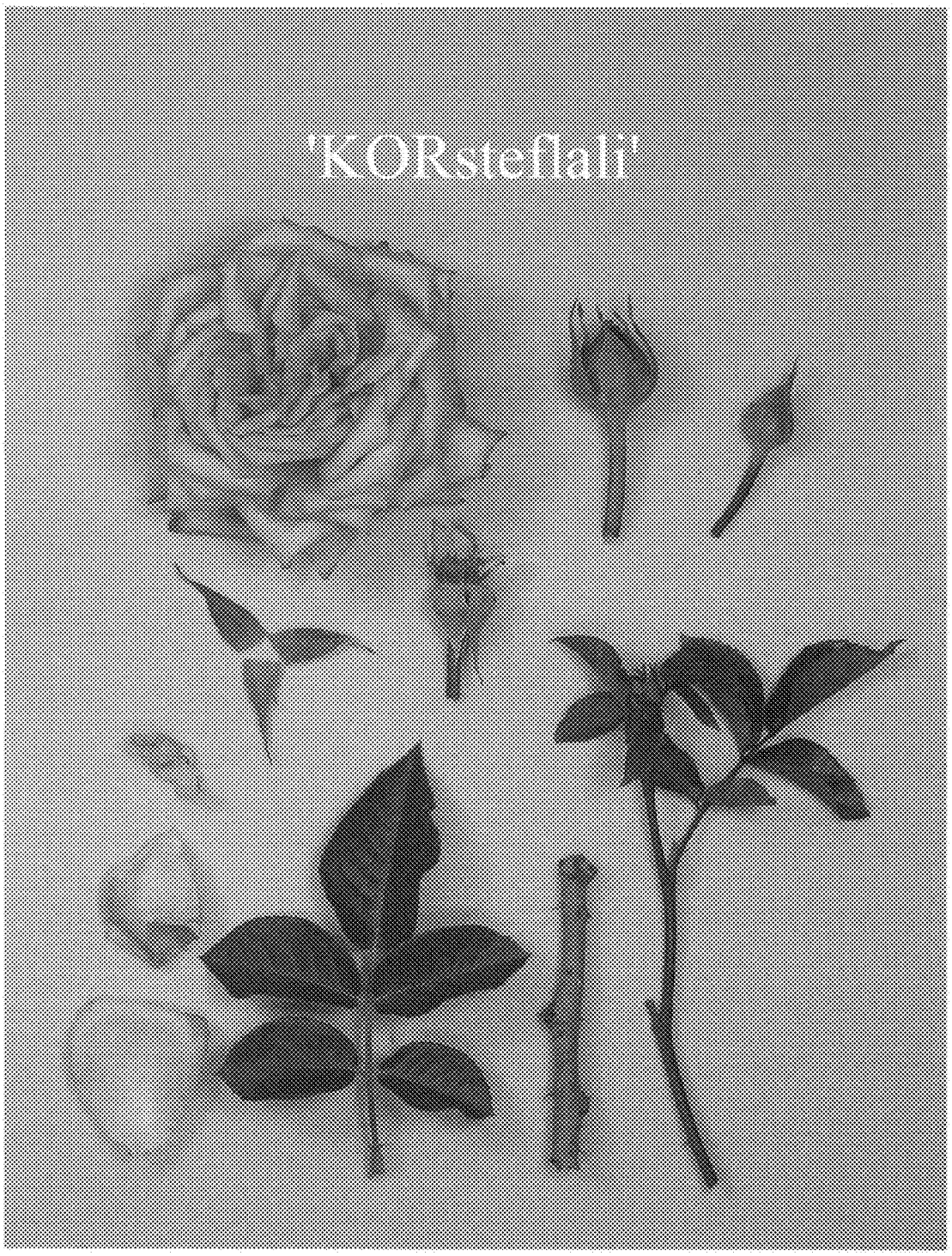
'KORsteflali'